United States Patent [19]
Woodbury et al.

[11] Patent Number: 6,066,758
[45] Date of Patent: May 23, 2000

[54] THIOGLYCEROL DERIVATIVES AND THEIR USE IN POLYSULFIDE COMPOSITIONS FOR OPTICAL MATERIAL

[75] Inventors: Richard P. Woodbury; John B. Stallman, both of Amherst, N.H.; George F. Winterson, Lowell, Mass.; Kenneth L. Avery, Merrimack, N.H.

[73] Assignee: Hampshire Chemical Corp., Lexington, Mass.

[21] Appl. No.: 09/388,518

[22] Filed: Sep. 2, 1999

Related U.S. Application Data

[63] Continuation-in-part of application No. 08/978,759, Nov. 26, 1997, Pat. No. 5,973,192.

[51] Int. Cl.⁷ .................................................. C07C 321/00

[52] U.S. Cl. ............................ 560/154; 528/77; 264/7.32

[58] Field of Search ..................................... 560/152, 154; 528/77; 264/7.32

[56] References Cited

U.S. PATENT DOCUMENTS

| | | | |
|---|---|---|---|
| 3,865,787 | 2/1975 | Ludwig et al. | 260/45.75 S |
| 4,689,387 | 8/1987 | Kajimoto et al. | 528/76 |
| 4,775,733 | 10/1988 | Kanemura et al. | 528/67 |
| 5,191,055 | 3/1993 | Kanemura et al. | 528/77 |
| 5,306,799 | 4/1994 | Kobayashi et al. | 528/77 |
| 5,326,501 | 7/1994 | Ohkubo et al. | 252/582 |
| 5,594,088 | 1/1997 | Nagata et al. | 528/77 |
| 5,652,321 | 7/1997 | Kawauchi et al. | 528/76 |
| B1 4,689,387 | 4/1996 | Kajimoto et al. | 528/76 |

FOREIGN PATENT DOCUMENTS 0 742 244  11/1996  European Pat. Off. .

*Primary Examiner*—Samuel Barts
*Attorney, Agent, or Firm*—Nields, Lemack & Dingman

[57] ABSTRACT

Novel thioglycerol derivatives, processes for their manufacture, and optical materials made from such compounds. The thioglycerol derivatives have high concentrations of sulfur relative to compounds conventionally used for optical materials, and thus exhibit high refractive indices without sacrificing processability.

4 Claims, No Drawings

THIOGLYCEROL DERIVATIVES AND THEIR USE IN POLYSULFIDE COMPOSITIONS FOR OPTICAL MATERIAL

This application is a continuation-in-part of U.S. patent application Ser. No. 08/978,759 filed Nov. 26, 1997 now U.S. Pat. No. 5,973,192.

BACKGROUND OF THE INVENTION

The present invention is directed to thioglycerol derivatives and their preparation, the derivatives having utility in optical materials such as lenses.

Plastic lenses for use in eyeglasses and cameras have become widespread in view of their lightweight, durability, dyeability and workability as compared to conventional glass lenses. Resin compositions suitable for the manufacture of optical lenses must possess certain characteristics, including a high refractive index, high surface accuracy, low dispersion properties and good heat resistance, impact resistance and scratch resistance. Diethylene glycol bis (allylcarbonate (DAC) and polycarbonates have conventionally been used for plastic lenses. Lenses made of DAC, however, have lower refractive indices than lenses made of glass of a corresponding overall thickness, and therefore do not perform as well in this regard.

U.S. Pat. Nos. 4,775,733 and 5,191,055 disclose polyurethane lenses made of a polymer between a xylylene diisocyanate compound and a polythiol compound having a higher refractive index than lenses made from DAC. However, such lenses generally suffer from poor heat resistance, hindering the ability to use high temperatures during heat treatment processing steps.

It therefore would be desirable to develop compositions for use in making optical materials that do not suffer from the various drawbacks mentioned above, and that have good machinability and processability.

SUMMARY OF THE INVENTION

The problems of the prior art have been overcome by the present invention, which provides novel thioglycerol derivatives, processes for their manufacture, and optical materials made from such compounds. The thioglycerol derivatives have high concentrations of sulfur relative to compounds conventionally used for optical materials, and thus exhibit high refractive indices without sacrificing important properties such as processability.

DETAILED DESCRIPTION OF THE INVENTION

Thioglycerol ($HSCH_2CH(OH)CH_2OH$) and 1,3-dimercapto-2-propanol are the bases of the compounds of the present invention. They can be conveniently esterified with common mercaptoacids of the formula $HS(CH_2)_n COOH$ wherein n is from 1 to 5, including thioglycolic acid, 3-mercaptopropionic acid, etc., to form compounds having the following generic formula:

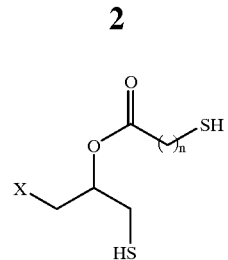

wherein X is —SH or X=—SH,

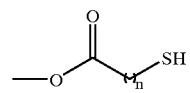

and n is from 1 to 5. Those skilled in the art will appreciate that as the chain length of the mercapto acid increases (i.e., as n increases from 1 to 5 and beyond), the percent sulfur in the composition decreases, thereby decreasing the refractive index of the resulting derivative. Accordingly, esterification with thioglycolic acid is especially preferred, in particular with two equivalents of thioglycolic acid, resulting in thioglycerol bismercaptoacetate (TGBMA) having the following formula:

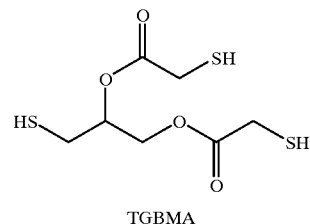

TGBMA

In addition, the resulting TGBMA derivative can be further oxidized, such as with peroxide or other suitable oxidizing agents known to those skilled in the art, to give varying degrees of disulfide. Such disulfides, which can include dimers, trimers and oligomers, can be represented by the following generic formula:

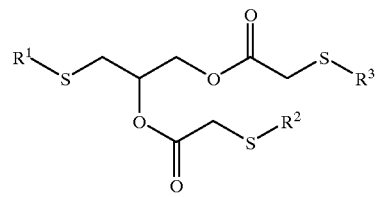

wherein $R_1$, $R_2$ and $R_3$ may be the same or different and are independently selected from hydrogen,

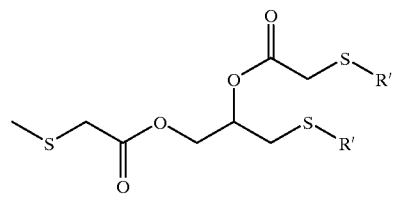

-continued
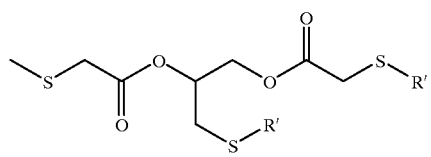
or
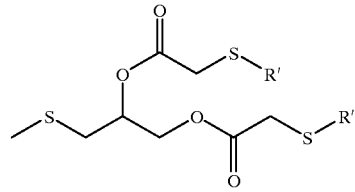
wherein R' is hydrogen or $R_1$. Examples of such disulfides are shown below:
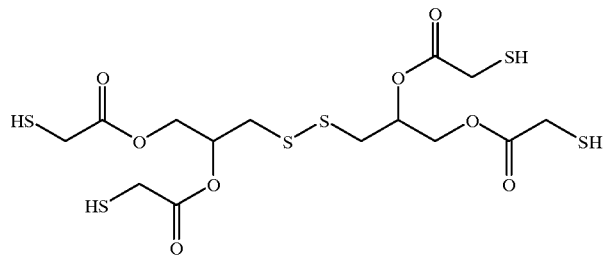
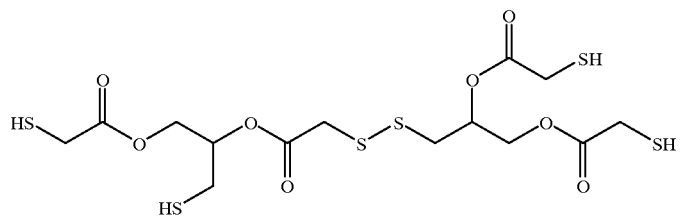
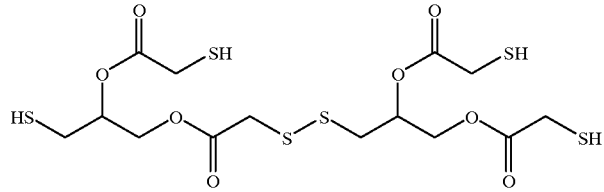
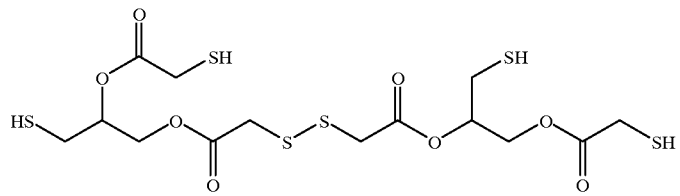
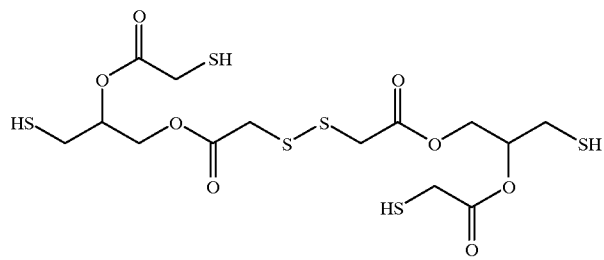
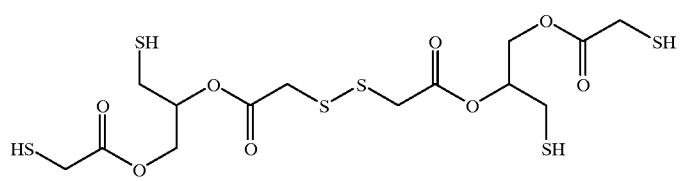

-continued

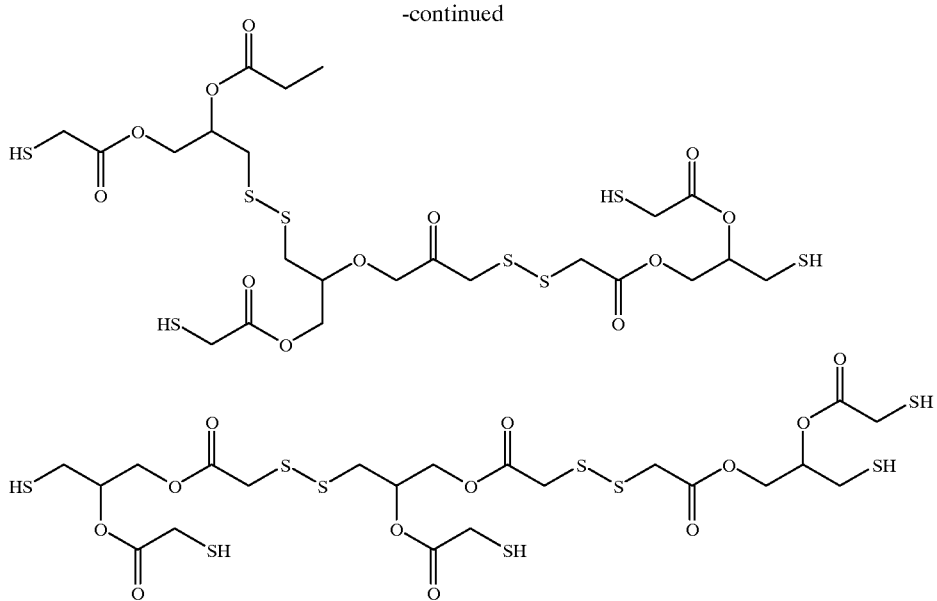

The trimers and oligomers are formed by further oxidation of the mercaptans of the dimers. The higher molecular weight materials result in an increase in the refractive index. Moreover, as the reaction medium continues to be heated, the refractive index increases. Accordingly, one can control the refractive index by controlling the heating of the reaction. The resulting product is a complex mixture of any of the foregoing structures.

The esterified product can be washed with a suitable base, preferably ammonia or alkali metal hydroxide, such as sodium or potassium hydroxide, to remove any residual mercaptoacid. The present inventors also have found that limiting the wash step also limits the refractive index of the final product. More specifically, washing the product with base, preferably ammonia, has a drammatic effect on the refractive index. Thus, by limiting the washing step, the refractive index can be kept at a predetermined level (if the refractive index is too high, the product is not compatible with other components).

In an alternative embodiment, thioglycerol is oxidized to the corresponding disulfide with a suitable oxidizing agent:

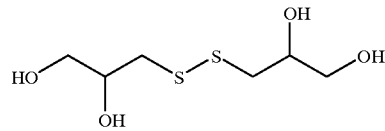

This resulting tetraol can be readily esterified with the aforementioned mercaptoacids to form a highly functionalized mercaptan having a sulfur content slightly higher than thioglycerol bismercaptoacetate:

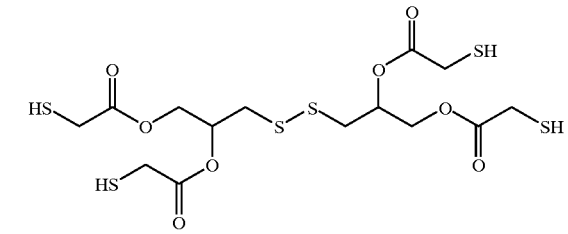

In a further embodiment of the present invention, 1,3-dimercapto-2-propanol is esterified with thioglycolic acid to produce dimercaptopropanol mercaptoacetate. Disulfides of this mercaptoacetate can be produced by analgous procedures to those above, resulting in the following derivatives:

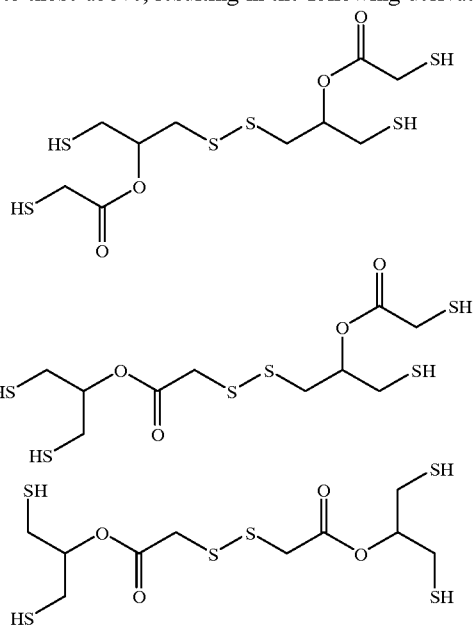

Optical materials such as lenses can be prepared from the derivatives of the present invention by conventional means. Suitable additives such as surface active agents may be used. The resulting lens may be subjected as necessary to various physical and chemical treatments such as surface polishing, treatment for antistaticity, hard coat treatment, non-reflecting coat treatment, dyeing, treatment for photochromism, etc., all well known to those skilled in the art.

The invention is further illustrated by the following non-limiting examples.

EXAMPLE 1

In a 5 liter, 3 neck roundbottom flask equipped with a magnetic stirrer, thermocouple and a distillation head with vacuum take off, is placed thioglycerol (1994.60 g, 7.78 moles) and thioglycolic acid (2332.96 g, 24.82 moles).

Methane sulfonic acid (14.16 g, 0.15 mole) is added, vacuum applied (5–10 mm Hg) and the reaction heated to 70° C. When the reaction temperature reached about 40° C., water began to distill over. The reaction was heated at 70° C. for 4–5 hours and cooled to room temperature. The reaction is then transferred to a 6 liter Erlenmeyer flask which is equipped with an overhead stirrer.

Aqueous ammonia (4218.00 g, 5%, 12.41 moles) was added and the reaction stirred for 30–45 minutes. An exotherm occurs to approximately 35–40° C. upon addition of the ammonia. This can be controlled by cooling the reaction to 10–15° C. prior to the addition of ammonia. The upper ammonia layer is then removed and the reaction washed with a 3×2 liters of water. After washing is completed, the reaction is stripped water free, either via a vacuum distillation or on the rotary evaporator to yield 1994.6 g, 69%, of TGBMA as a light yellow oil. The refractive index was 1.5825.

EXAMPLE 2

To a 250 ml, three neck flask equipped with a condenser, thermometer, magnetic stirring, and a constant addition funnel was added thioglycerol (42.00 g, 0.39 mole), water (32.40 g, 1.80 mole) and ferrous sulfate (0.02 g, 0.3 mmole). Hydrogen peroxide (42.00 g, 0.30 moles) was added slowly, maintaining a temperature of less than 50° C. Care was taken not to add the hydrogen peroxide too rapidly, thereby avoiding the accumulation of excess peroxide.

The reaction mixture was extracted with methyl isobutyl ketone to remove unreacted thioglycerol. The aqueous portion was concentrated to dryness, after testing for unreacted peroxide, resulting in 41.90 g of the disulfide product (>99% yield). The refractive index was 1.5670.

EXAMPLE 3

Dithioglycerol tetramercaptoacetate was prepared using the procedure described in Example 1 after adjusting the stoichiometry.

EXAMPLE 4

1,3-Dimercapto-2-propanol (12.8 g, 0.1 moles), thioglycolic acid (9.5 g, 0.1 moles) and methane sulfonic acid (0.13 g, 1.30 mmoles) were combined and heated to 70° C. under about 4 mm of vacuum. The reaction mixture was held at this temperature and pressure for 2–3 hours until the water was distilled from the reaction. The reaction completion can be monitored by titration for acid number.

The reaction was washed with a 3.7% aqueous ammonia followed by one or two water washed to remove the excess thioglycolic acid. The final product was stripped to dryness resulting in a 79% yield. The refractive index was 1.6200.

EXAMPLE 5

In a 5 liter, 3 neck round bottom flask equipped with a magnetic stirrer, thermocouple and a distillation head with vacuum take off, is placed thioglycerol (1000.00 g, 9.26 moles), thioglycolic acid (1874.07 g, 20.37 moles) and methane sulfonic acid (11.52 g, 0.12 moles). Vacuum is applied (5–10 mm Hg) and the reaction heated to 70° C. The reaction was heated at 70° C. for 3–4 hours at which time the crude refractive index is 1.5500. After additional heating for 2–3 hours, which raises the crude refractive index to 1.5610, the reaction is cooled and transferred to a 6 liter Erlenmeyer flask equipped with an overhead stirrer.

Aqueous ammonima (2361.3 g, 5%, 6.95 moles) was added to the Erlenmeyer flask and the reaction stirred for 30–60 minutes. An exotherm occurs to approximately 35–40° C. upon addition of ammonia, Cooling the reaction to 10–15° C. prior to ammonia addition can control the exotherm. The upper ammonia layer is then removed and the reaction washed with 3×2 liters of water. After washing is completed, the reaction is stripped water free, either by vacuum distillation or rotary evaporator to yield 1777.9 g, 75% of TGBMA as a light yellow oil. The refractive index has now increased to 1.5825 from the crude refractive index of 1.5610.

What is claimed is:

1. A thioglycerol derivative having the following formula:

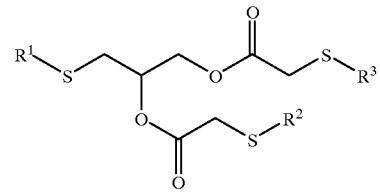

wherein $R_1$, $R_2$ and $R_3$ may be the same or different and are independently selected from hydrogen,

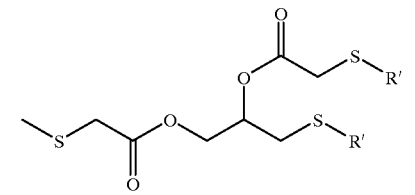

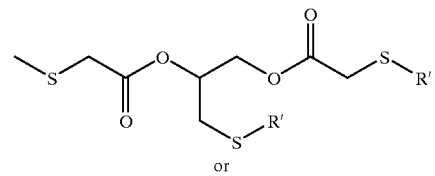

or

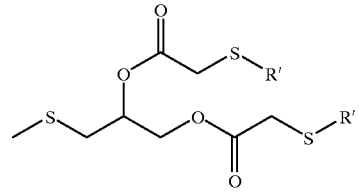

wherein R' is hydrogen or $R_1$, with the proviso that $R_1$, $R_2$ and $R_3$ do not all represent hydrogen.

2. A thioglycerol derivative selected from the group consisting of the following compounds or a mixture thereof:

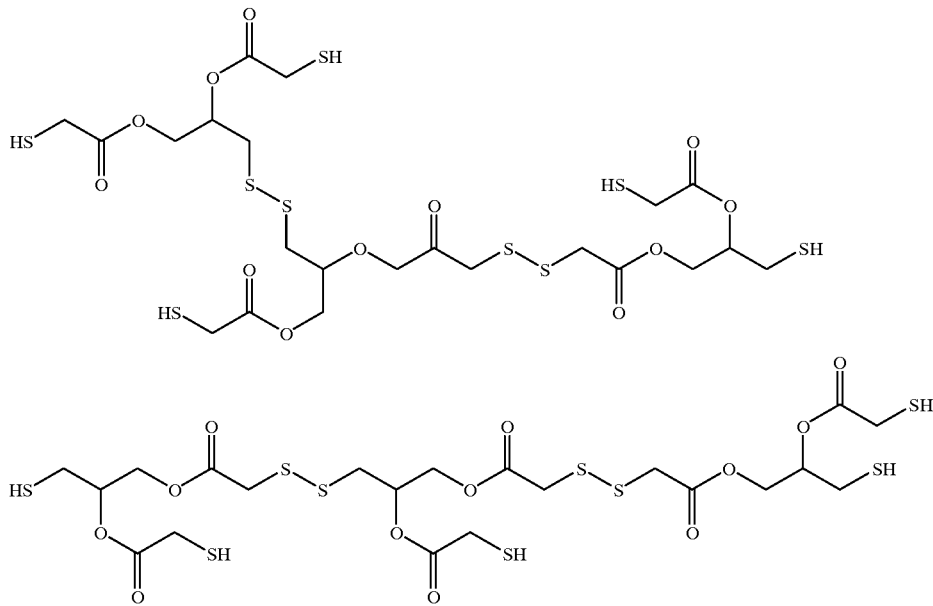
3. A plastic lens comprising the thioglycerol derivative of claim 1.
4. A plastic lens comprising the thioglycerol derivative of claim 2.
* * * * *